(12) United States Patent
Soejima et al.

(10) Patent No.: US 10,371,769 B2
(45) Date of Patent: Aug. 6, 2019

(54) MRI APPARATUS AND METHOD USING DIRECT A/D OF MR SIGNALS WITHOUT FREQUENCY DOWN CONVERSION

(71) Applicant: TOSHIBA MEDICAL SYSTEMS CORPORATION, Otawara-shi, Tochigi (JP)

(72) Inventors: Kazuyuki Soejima, Tochigi (JP); Sojuro Kato, Tochigi (JP); Makoto Hirama, Tochigi (JP)

(73) Assignee: TOSHIBA MEDICAL SYSTEMS CORPORATION, Otawara-Shi, Tochigi-Ken (JP)

( * ) Notice: Subject to any disclaimer, the term of this patent is extended or adjusted under 35 U.S.C. 154(b) by 1037 days.

(21) Appl. No.: 14/738,276

(22) Filed: Jun. 12, 2015

(65) Prior Publication Data
US 2015/0276910 A1 Oct. 1, 2015

Related U.S. Application Data

(63) Continuation of application No. PCT/JP2013/083701, filed on Dec. 17, 2013.

(30) Foreign Application Priority Data

Dec. 18, 2012 (JP) .................................. 2012-276289
Oct. 23, 2013 (JP) .................................. 2013-219895

(51) Int. Cl.
*G01R 33/36* (2006.01)
(52) U.S. Cl.
CPC ................................ *G01R 33/3621* (2013.01)
(58) Field of Classification Search
USPC .......................... 324/300–322; 600/407–435; 382/128–131
See application file for complete search history.

(56) References Cited

U.S. PATENT DOCUMENTS 5,436,600 A * 7/1995 Van Heteren ...... G01R 33/3607
324/314
6,653,833 B2 11/2003 Baumgartl et al.
(Continued)

FOREIGN PATENT DOCUMENTS

JP 8-164119 6/1996
JP 10-165392 6/1998
(Continued)

OTHER PUBLICATIONS

Notification of Transmittal of Translation of the International Preliminary Report on Patentability in PCT/JP2013/083701 dated Jul. 2, 2015.

(Continued)

*Primary Examiner* — Melissa J Koval
*Assistant Examiner* — Tiffany A Fetzner
(74) *Attorney, Agent, or Firm* — Nixon & Vanderhye P.C.

(57) ABSTRACT

According to one embodiment, a magnetic resonance imaging apparatus includes a static field magnet, a gradient coil, at least one radio frequency coil, a receiver and processing circuitry. The static field magnet, the gradient coil, the at least one radio frequency coil and the receiver are configured to acquire magnetic resonance signals from an object. The processing circuitry is configured to generate magnetic resonance image data based on the magnetic resonance signals. The receiver is configured to convert analog magnetic resonance signals received by the at least one radio frequency coil into digital magnetic resonance signals without a downconversion; separate the digital magnetic resonance signals into in-phase signals and quadrature-phase signals; and perform filter processing for removing noises of the in-phase signals and the quadrature-phase signals.

14 Claims, 9 Drawing Sheets

(56) References Cited

U.S. PATENT DOCUMENTS

| | | |
|---|---|---|
| 7,106,064 B2 | 9/2006 | Yoshizawa |
| 7,977,945 B2 | 7/2011 | Baumgartl et al. |
| 8,049,505 B2 * | 11/2011 | Van Liere .......... H03H 17/0642 |
| | | 324/318 |
| 8,457,579 B2 * | 6/2013 | Mishali ................ H04B 1/0092 |
| | | 455/130 |
| 8,575,935 B2 | 11/2013 | Roeven |
| 9,910,112 B2 * | 3/2018 | Soejima ............. G01R 33/3621 |
| 2010/0001725 A1 * | 1/2010 | Van Liere .......... G01R 33/3621 |
| | | 324/307 |
| 2015/0015256 A1 * | 1/2015 | Soejima ............. G01R 33/3621 |
| | | 324/309 |
| 2015/0276910 A1 * | 10/2015 | Soejima ............. G01R 33/3621 |
| | | 324/309 |

FOREIGN PATENT DOCUMENTS

| | | |
|---|---|---|
| JP | 2002-159470 | 6/2002 |
| JP | 2005-131102 | 5/2005 |
| JP | 2006-017486 | 1/2006 |
| JP | 2011-505498 | 3/2011 |
| JP | 2011-206287 | 10/2011 |

OTHER PUBLICATIONS

First Japanese office action dated Oct. 3, 2017, in Patent Application No. 2013-219895.
International Search Report and Written Opinion for PCT/JP2013/083701 dated Mar. 4, 2014, seven pages.

\* cited by examiner

US 10,371,769 B2

MRI APPARATUS AND METHOD USING DIRECT A/D OF MR SIGNALS WITHOUT FREQUENCY DOWN CONVERSION

CROSS REFERENCES TO RELATED APPLICATIONS

This is a continuation of Application PCT/JP2013/083701, filed on Dec. 17, 2013.

This application is based upon and claims the benefit of priorities from Japanese Patent Application No. 2012-276289 filed on Dec. 18, 2012 and Japanese Patent Application No. 2013-219895 filed on Oct. 23, 2013; the entire contents of Japanese Patent Application No. 2012-276289 and Japanese Patent Application No. 2013-219895 are incorporated herein by reference.

FIELD

Embodiments described herein relate generally to an MRI (magnetic resonance imaging) apparatus and a magnetic resonance imaging method.

BACKGROUND

The MRI apparatus is an imaging diagnostic apparatus which magnetically excites nuclear spins of an object set in a static magnetic field with RF (radio frequency) signals having the Larmor frequency and reconstructs images based on NMR (nuclear magnetic resonance) signals generated due to the excitation.

In the MRI apparatus, a direct sampling method for detection processing of MR signals is proposed. The direct sampling method is a signal processing method, which applies A/D (analog to digital) conversion directly to analog signals without any frequency conversion, for a detection. When MR signals are directly sampled, digital signals are detected using detection carriers of MR signals, produced by a DDS (direct digital synthesizer). The DDS is a circuit which digitally generates an arbitrary waveform and/or a frequency.

It is important to reduce noises and errors, which are superimposed on MR signals, in order to generate MR images with high quality.

Accordingly, an object of the present invention is to provide a magnetic resonance imaging apparatus and a magnetic resonance imaging method which can obtain MR signals, in which noises, errors or the like have been further reduced, when the MR signals are received by the direct sampling method.

DETAILED DESCRIPTION

Figure 1:
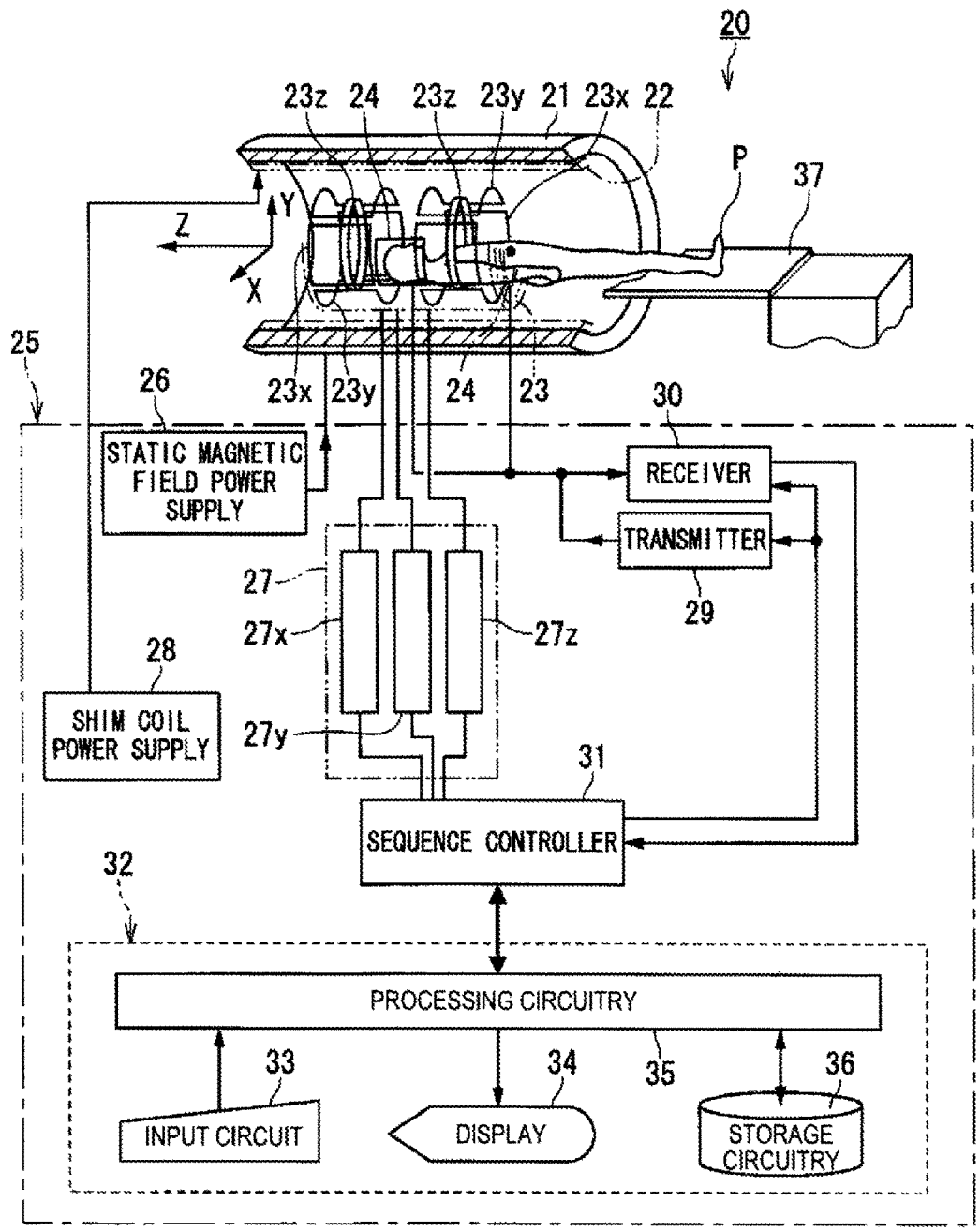
FIG. 1 is a block diagram showing a magnetic resonance imaging apparatus according to the first embodiment of the present invention.

In general, according to one embodiment, a magnetic resonance imaging apparatus includes a static field magnet, a gradient coil, at least one radio frequency coil, a receiver and processing circuitry. The static field magnet, the gradient coil, the at least one radio frequency coil and the receiver are configured to acquire magnetic resonance signals from an object. The processing circuitry is configured to generate magnetic resonance image data based on the magnetic resonance signals. The receiver is configured to convert analog magnetic resonance signals received by the at least one radio frequency coil into digital magnetic resonance signals without a downconversion; separate the digital magnetic resonance signals into in-phase signals and quadrature-phase signals; and perform filter processing for removing noises of the in-phase signals and the quadrature-phase signals.

Further, according to another embodiment, a magnetic resonance imaging apparatus includes a static field magnet, a gradient coil, at least one radio frequency coil, a receiver and processing circuitry. The static field magnet, the gradient coil, the at least one radio frequency coil and the receiver are configured to acquire magnetic resonance signals from an object. The processing circuitry is configured to generate magnetic resonance image data based on the magnetic resonance signals. The receiver is configured to convert analog magnetic resonance signals received by the at least one radio frequency coil into digital magnetic resonance signals without a downconversion, and correct an phase error of a clock of a detection carrier for each magnetic resonance signal, out of the digital magnetic resonance signals, corresponding to a radio frequency transmission signal whose a clock of a transmission carrier is generated in a method other than a method by a direct digital synthesizer. The clock of the detection carrier is generated by the direct digital synthesizer. The phase error is corrected based on a clock generated in the method other than the method by the direct digital synthesizer.

Further, according to another embodiment, a magnetic resonance imaging method includes: acquiring magnetic resonance signals from an object; and generating magnetic resonance image data based on the magnetic resonance signals. The generating the magnetic resonance image data includes: converting analog magnetic resonance signals received by at least one radio frequency coil into digital magnetic resonance signals without a downconversion; separating the digital magnetic resonance signals into in-phase signals and quadrature-phase signals; and performing filter processing for removing noises of the in-phase signals and the quadrature-phase signals.

Further, according to another embodiment, a magnetic resonance imaging method includes: acquiring magnetic resonance signals from an object; and generating magnetic resonance image data based on the magnetic resonance signals. The generating the magnetic resonance image data includes: converting analog magnetic resonance signals received by at least one radio frequency coil into digital magnetic resonance signals without a downconversion; and correcting an phase error of a clock of a detection carrier for each magnetic resonance signal, out of the digital magnetic resonance signals, corresponding to a radio frequency transmission signal whose a clock of a transmission carrier is generated in a method other than a method by a direct digital synthesizer. The clock of the detection carrier is generated by the direct digital synthesizer. The phase error is corrected based on a clock generated in the method other than the method by the direct digital synthesizer.

A magnetic resonance imaging apparatus and a magnetic resonance imaging method according to embodiments of the present invention will be described with reference to the accompanying drawings.

First Embodiment

FIG. 1 is a block diagram showing a magnetic resonance imaging apparatus according to the first embodiment of the present invention.

A magnetic resonance imaging apparatus 20 includes a cylinder-shaped static field magnet 21, a shim coil 22, a gradient coil 23 and RF coils 24. The static field magnet 21 generates a static magnetic field. The shim coil 22 is arranged inside the static field magnet 21.

The magnetic resonance imaging apparatus 20 also includes a control system 25. The control system 25 includes a static magnetic field power supply 26, a gradient power supply 27, a shim coil power supply 28, a transmitter 29, a receiver 30, a sequence controller 31 and a computer 32. The gradient power supply 27 of the control system 25 includes an X-axis gradient power supply 27$x$, a Y-axis gradient power supply 27$y$ and a Z-axis gradient power supply 27$z$. The computer 32 includes an input circuit 33, a display 34, processing circuitry 35 and a storage circuitry 36.

The static field magnet 21 communicates with the static magnetic field power supply 26. The static magnetic field power supply 26 supplies electric current to the static field magnet 21 to generate a static magnetic field in an imaging region. The static field magnet 21 includes a superconductivity coil in many cases. The static field magnet 21 gets current from the static magnetic field power supply 26 which communicates with the static field magnet 21 at excitation. However, once excitation has been made, the static field magnet 21 is usually isolated from the static magnetic field power supply 26. The static field magnet 21 may include a permanent magnet which makes the static magnetic field power supply 26 unnecessary.

The static field magnet 21 has the cylinder-shaped shim coil 22 coaxially inside itself. The shim coil 22 communicates with the shim coil power supply 28. The shim coil power supply 28 supplies current to the shim coil 22 so that the static magnetic field becomes uniform.

The gradient coil 23 includes an X-axis gradient coil 23$x$, a Y-axis gradient coil 23$y$ and a Z-axis gradient coil 23$z$. Each of the X-axis gradient coil 23$x$, the Y-axis gradient coil 23$y$ and the Z-axis gradient coil 23$z$, which is cylinder-shaped, is arranged inside the static field magnet 21. The gradient coil 23 has also a bed 37 in the area formed inside it which is an imaging area. The bed 37 supports an object P. The RF coils 24 include a WBC (whole body coil), which is built in a gantry, for transmission and reception of RF signals and local coils, which are arranged around the bed 37 or the object P, for reception of RF signals.

The gradient coil 23 communicates with the gradient power supply 27. The X-axis gradient coil 23$x$, the Y-axis gradient coil 23$y$ and the Z-axis gradient coil 23$z$ of the gradient coil 23 communicate with the X-axis gradient power supply 27$x$, the Y-axis gradient power supply 27$y$ and the Z-axis gradient power supply 27$z$ of the gradient power supply 27 respectively.

The X-axis gradient power supply 27$x$, the Y-axis gradient power supply 27$y$ and the Z-axis gradient power supply 27$z$ supply currents to the X-axis gradient coil 23$x$, the Y-axis gradient coil 23$y$ and the Z-axis gradient coil 23$z$ respectively so as to generate gradient magnetic fields Gx, Gy and Gz in the X, Y and Z directions in the imaging area.

The RF coils 24 communicate with the transmitter 29 and/or the receiver 30. The transmission RF coil 24 transmits RF signals given from the transmitter 29 to the object P. The reception RF coil 24 receives MR signals generated due to nuclear spins inside the object P which are excited by the RF signals to give to the receiver 30.

The sequence controller 31 of the control system 25 communicates with the gradient power supply 27, the transmitter 29 and the receiver 30. The sequence controller 31 stores sequence information describing control information needed in order to drive the gradient power supply 27, the transmitter 29 and the receiver 30, and generates gradient magnetic fields Gx, Gy and Gz in the X, Y and Z directions and RF signals by driving the gradient power supply 27, the transmitter 29 and the receiver 30 according to a predetermined stored sequence. The above-described control information includes motion control information, such as intensities, application durations and application timings of electric current pulses which should be applied to the gradient power supply 27.

The sequence controller 31 is also configured to give raw data to the computer 32. The raw data, which are complex-valued data, are generated by the receiver 30 performing detection and A/D conversion of NMR signals.

The transmitter 29 gives RF signals to the RF coil 24 in accordance with control information provided from the sequence controller 31. Meanwhile, the receiver 30 performs detection, necessary signal processing and A/D conversion of NMR signals given from the RF coils 24 to generate raw data which are digitized complex-valued data. The generated raw data are given from the receiver 30 to the sequence controller 31.

The processing circuitry 35 has various functions by executing programs stored in the storage circuitry 36 of the computer 32. The processing circuitry 35 can consist of a single circuit or plural circuits.

Specifically, the processing circuitry 35 has a function to set imaging conditions including a pulse sequence and output the imaging conditions to the sequence controller 31, a function to generate MR image data by performing image reconstruction processing, including an FT (Fourier transform), of MR signals output from the sequence controller 31, and a function to perform various image processing of MR image data. That is, the processing circuitry 35 has a function as an image generation system which generates MR image data based on MR signals.

Next, a detailed configuration and detailed functions of the receiver 30 will be described. The receiver 30 is configured to sample MR signals by direct sampling in which MR signals received by the RF coils 24 for reception are subjected to A/D conversion without performing a frequency conversion.

Figure 2:
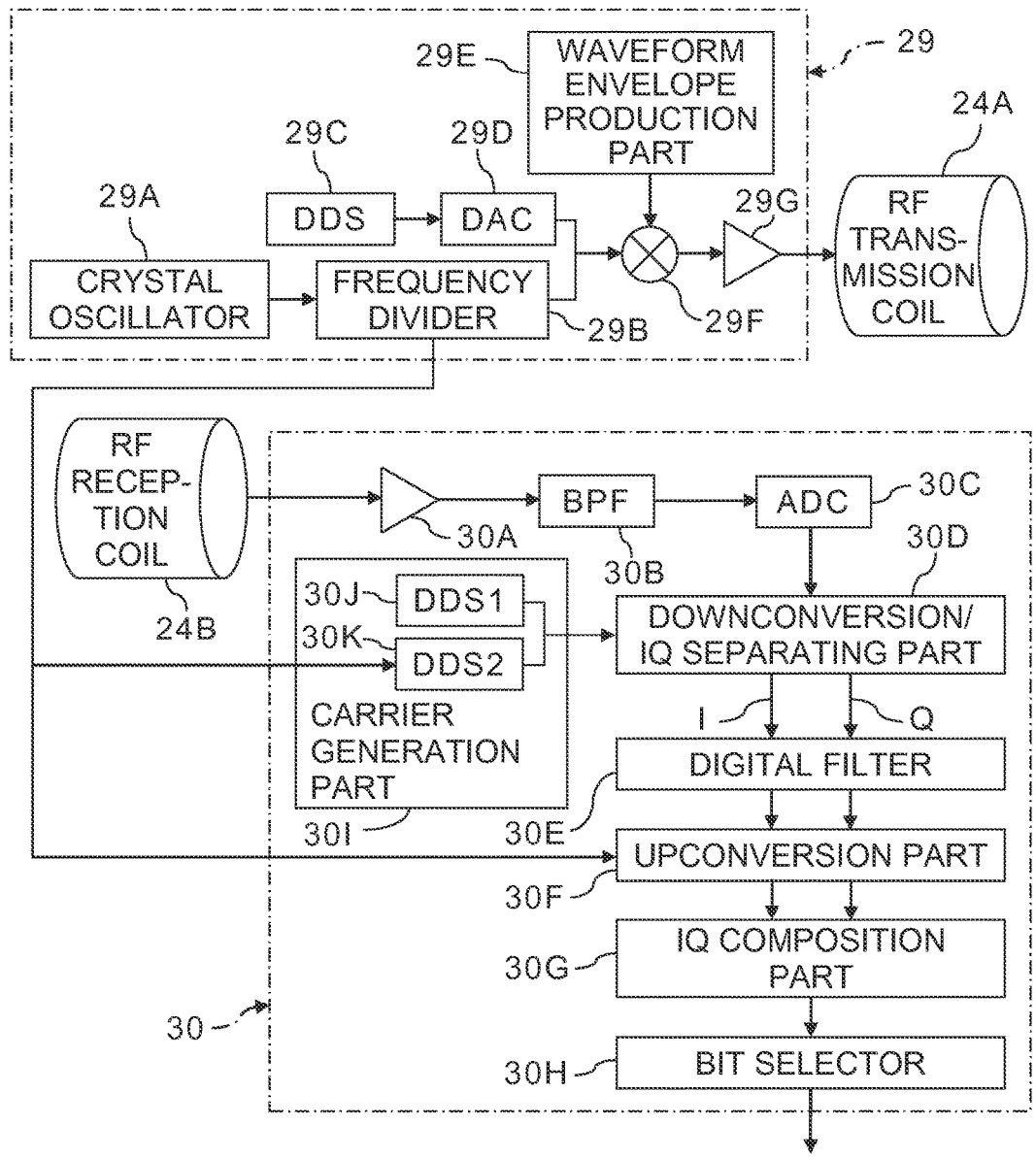
FIG. 2 is a functional block diagram showing each detailed configuration of the transmitter and the receiver which are shown in FIG. 1.

FIG. 2 is a functional block diagram showing each detailed configuration of the transmitter 29 and the receiver 30 which are shown in FIG. 1.

The transmitter 29 has a crystal oscillator 29A, a frequency divider 29B, a DDS 29C, a DAC (digital to analog converter) 29D, a waveform envelope production part 29E, a mixer 29F and an amplifier 29G.

An analog clock signal generated with the crystal oscillator 29A as the original oscillation is divided into analog clock signals, which have predetermined frequencies, in the frequency divider 29B. Meanwhile, a clock signal having a frequency different from a frequency of clock signal generated in the frequency divider 29B, for example a clock signal having a higher frequency, is generated as a digital signal in the DDS 29C. The clock signal generated in the DDS 29C is converted into an analog clock signal in the DAC 29D, and is output to the mixer 29F with a clock signal generated in the frequency divider 29B as a transmission carrier.

On the other hand, an analog waveform signal which has an envelope produced in the waveform envelope production part 29E is output to the mixer 29F. Thereby, the waveform signal is subjected to a frequency modulation by a transmission carrier in the mixer 29F. The modulated waveform signal is amplified in the amplifier 29G as an RF transmission signal, and subsequently, the amplified waveform signal is output to an RF transmission coil 24A.

Meanwhile, the receiver 30 has an amplifier 30A, a BPF (band pass filter) 30B, an ADC (A/D converter) 30C, a downconversion/IQ separating part 30D, a digital filter 30E, an upconversion part 30F, an IQ composition part 30G, a bit selector 30H and a carrier generation part 30I for reception detection. The carrier generation part 30I for reception detection can be further configured with the first DDS 30J and the second DDS 30K. Among these elements configuring the receiver 30, elements, such as the downconversion/IQ separating part 30D, the digital filter 30E, the upconversion part 30F, the IQ composition part 30G, the bit selector 30H and the carrier generation part 30I, to process digital signals can be configured by installing programs to processing circuitry consisting of a single circuit or plural circuits. Note that, the processing circuitry of the receiver 30 may be integrated with the processing circuitry 35 having the function as the image generation system which generates MR image data.

MR signals received by each RF reception coil 24B are amplified in the amplifier 30A and are input into the BPF 30B. The analog MR signals whose frequency band has been limited in the BPF 30B are converted into digital signals in the ADC 30C without any frequency conversion. That is, MR signals are directly sampled in the receiver 30.

Each MR signal after the AD conversion is down-converted to a signal having a frequency in a baseband and is separated into an I (in-phase) signal and a Q (quadrature-phase) signal, in the downconversion/IQ separating part 30D. Specifically, carriers for reception detections of an I signal and a Q signal generated in the carrier generation part 30I for reception detection are output to the downconversion/IQ separating part 30D, and each MR signal after the AD conversion is demodulated by a mixer.

In the carrier generation part 30I for reception detection, the first DDS 30J and the second DDS 30K generate carriers for reception detections as digital signals by frequency. In the first DDS 30J, a carrier for reception detection having the same frequency as the frequency of the transmission carrier generated in the DDS 29C of the transmitter 29 is generated. Meanwhile, in the second DDS 30K, a carrier for reception detection having the same frequency as the frequency of the transmission carrier generated in the frequency divider 29B of the transmitter 29 is generated.

The transmission carrier generated as a digital signal in the DDS 29C of the transmitter 29 does not come from the crystal oscillator 29A as the original oscillation. Therefore, errors arise in a frequency and a phase of the transmission carrier generated in the DDS 29C, against a frequency and a phase of the transmission carrier in a lower frequency side generated as an analog signal in the frequency divider 29B.

However, the carrier for reception detection in a higher frequency side generated in the first DDS 30J is generated as a digital signal, in the same method as the generation method of the transmission carrier in the DDS 29C of the transmitter 29, without using the crystal oscillator 29A as the original oscillation. Therefore, an error of the carrier for reception detection generated in the first DDS 30J and an error of the transmission carrier generated in the DDS 29C of the transmitter 29 are equivalent to each other. Therefore, the error of the transmission carrier generated in the DDS 29C is offset by the error of the carrier for reception detection generated in the first DDS 30J. As a result, the first DDS 30J can generate a carrier for reception detection at an appropriate timing corresponding to the transmission carrier.

Meanwhile, the carrier for reception detection in a lower frequency side generated in the second DDS 30K does not come from the crystal oscillator 29A as the original oscillation, either. Therefore, errors arise in a frequency and a phase of the carrier for reception detection generated in the second DDS 30K, against a frequency and a phase of the transmission carrier generated in the frequency divider 29B Accordingly, the second DDS 30K is configured to obtain an analog clock signal from the frequency divider 29B and to reset a phase of the carrier for reception detection to an initial value, such as zero, so as to correct errors in a frequency and a phase, accumulated in the carrier for reception detection, based on the obtained clock signal. Thereby, the second DDS 30K can also generate a carrier for reception detection at an appropriate timing corresponding to the transmission carrier.

That is, the receiver 30 which composes the MR data acquiring system functions as a correction part configured to correct phase errors in clocks of respective detection carriers, whose clock are generated using a DDS and which are for an I signal and a Q signal corresponding to an RF transmission signal whose clock of a transmission carrier is generated by a frequency dividing of a clock generated using the crystal oscillator 29A as the original oscillation. Each of the phase errors in the clocks of the respective detection carriers can be corrected based on a clock generated in the frequency dividing of the clock generated using the crystal oscillator 29A as the original oscillation.

Then, the carrier generation part 30I for reception detection is configured to output carriers for reception detections after the above-mentioned phase correction to the downconversion/IQ separating part 30D. Therefore, reception detections of an I signal and a Q signal are performed using the carriers for reception detections after the phase correction, in the downconversion/IQ separating part 30D.

The I signals and Q signals which are output from the downconversion/IQ separating part 30D are output to the digital filter 30E. In the digital filter 30E, filter processing for noise removal is performed on each I signal and each Q signal separately. For the filter processing of the I signals and Q signals, a common filter is used. As a specific example, the filter processing can use an LPF (low pass filter), such as an FIR (finite impulse response) filter.

Each I signal and Q signal after the filter processing are up-converted into an intermediate frequency in the upconversion part 30F, and subsequently, combined with each other in the IQ composition part 30G. Then, each MR signal is output from the IQ composition part 30G to elements, such as the sequence controller 31, through the bit selector 30H.

As described above, the receiver 30 which composes the data acquiring system of MR signals has functions as a conversion part configured to convert analog MR signals received in the RF reception coils 24B into digital MR signals without any downconversion; a separating part configured to separate the digital MR signals into I signals and Q signals each down-converted into a baseband; and a filter processing part configured to perform filter processing, using a common filter for removing a noise, on each I signal and each Q signal, respectively. Furthermore, the receiver 30 has a function as a composition part configured to up-convert the filter processed I signal and the filter processed Q signal into a predetermined frequency and combine the up-converted I signal with the up-converted Q signal.

Next, an operation and action of the magnetic resonance imaging apparatus 20 will be described.

Firstly, an object P is set on the bed 37, and the static magnetic field is generated in an imaging area of the magnet 21 (a superconducting magnet), for the static magnetic field, excited by the static magnetic field power supply 26. Further, the shim coil power supply 28 supplies current to the shim coil 22, thereby uniformizing the static magnetic field generated in the imaging area.

Then, an imaging scan of the object P is performed. Specifically, the data acquiring system consisting of elements, such as the sequence controller 31 and the static field magnet 21, of the magnetic resonance imaging apparatus 20, to perform a scan, acquires MR signals from the object P according to imaging conditions including a pulse sequence set in the processing circuitry 35.

More specifically, the sequence controller 31 drives the gradient power supply 27, the transmitter 29 and the receiver 30 in accordance with the imaging conditions. Thereby, gradient magnetic fields are generated in the imaging area having the set object P, and RF signals are generated from the RF transmission coil 24A. Consequently, the RF reception coils 24B receive MR signals generated due to magnetic resonance in the object P. Then, the receiver 30 receives the MR signals from the RF reception coils 24B and performs detection processing of the MR signals by the direct sampling method.

Specifically, analog MR signals received by the RF reception coils 24B are amplified in the amplifier 30A. Then, the analog MR signals are input into the ADC 30C through the BPF 30B. A frequency band of each analog MR signal is limited in the BPF 30B. A frequency band $\Delta f_{BPF}$ of the BPF 30B is set to satisfy $\Delta f_{BPF} < 4f_s - 4f_0 - \Delta f_{MR}$ and $\Delta f_{BPF} < 4f_0 - 2f_s - \Delta f_{MR}$ under a condition of $f_s/2 + \Delta f_{MR}/4 < f_0 < f_s - \Delta f_{MR}/4$, wherein $\Delta f_{MR}$ is each frequency band of the analog MR signals input into the BPF 30B, $f_0$ is each center frequency of the analog MR signals, and $f_s$ is a sampling frequency.

Figure 3:
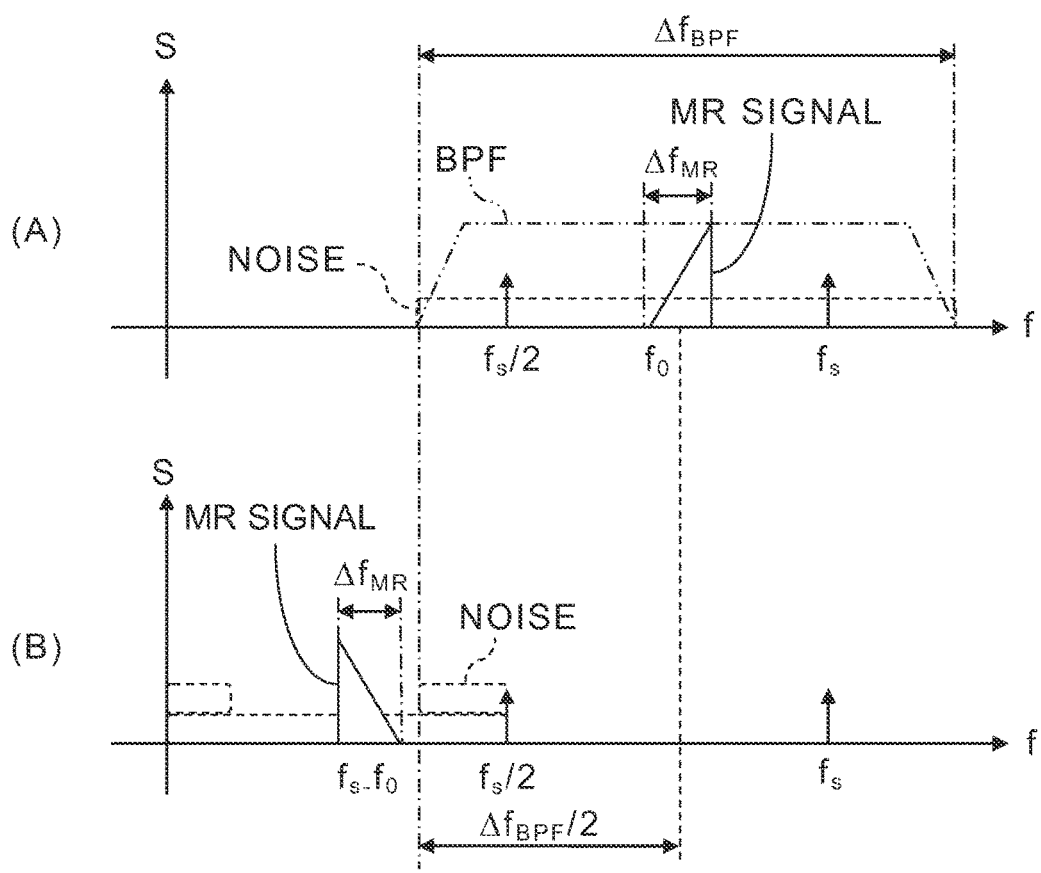
FIG. 3 shows a change of a noise, superimposed on an MR signal sampled with filter processing by the BPF shown in FIG. 2, before and after sampling the MR signal.

FIG. 3 shows a change of a noise, superimposed on an MR signal sampled with filter processing by the BPF 30B shown in FIG. 2, before and after sampling the MR signal.

In (A) and (B) of FIG. 3, each vertical axis shows signal amplitude S, and each horizontal axis shows frequency f. (A) of FIG. 3 shows an MR signal before sampling the MR signal in the ADC 30C, and (B) of FIG. 3 shows the MR signal after sampling the MR signal in the ADC 30C.

As shown in (A) of FIG. 3, in a case that an analog MR signal whose center frequency is $f_0$ and frequency band is $\Delta f_{MR}$ is sampled by a sampling frequency $f_s$, when filter processing of the MR signal is performed in the BPF 30B of which a frequency band $\Delta f_{BPF}$ becomes $\Delta f_{BPF} < 4f_s - 4f_0 - \Delta f_{MR}$ and $\Delta f_{BPF} < 4f_0 - 2f_s - \Delta f_{MR}$ under a condition of $f_s/2 + \Delta f_{MR}/4 < f_0 < f_s - \Delta f_{MR}/4$, a frequency band of a noise is limited to the frequency band $\Delta f_{BPF}$ of the BPF 30B.

Therefore, even when the noise is amplified by aliasing at the Nyquist frequency $f_s/2$, as shown in (B) of FIG. 3, it is possible to prevent the folded noise from superimposing on the MR signal whose frequency band is $\Delta f_{MR}$ and center frequency has become $f_s - f_0$. That is, the filter processing by the BPF 30B disposed in the fore stage of the ADC 30C can prevent an increase in a noise floor due to aliasing at the time of under sampling in which an analog MR signal does not fulfill the Nyquist condition with regard to a sampling frequency in the ADC 30C.

Each MR signal subjected to the AD conversion in the ADC 30C is down-converted and separated into an I signal and a Q signal, in the downconversion/IQ separating part 30D.

Figure 4:
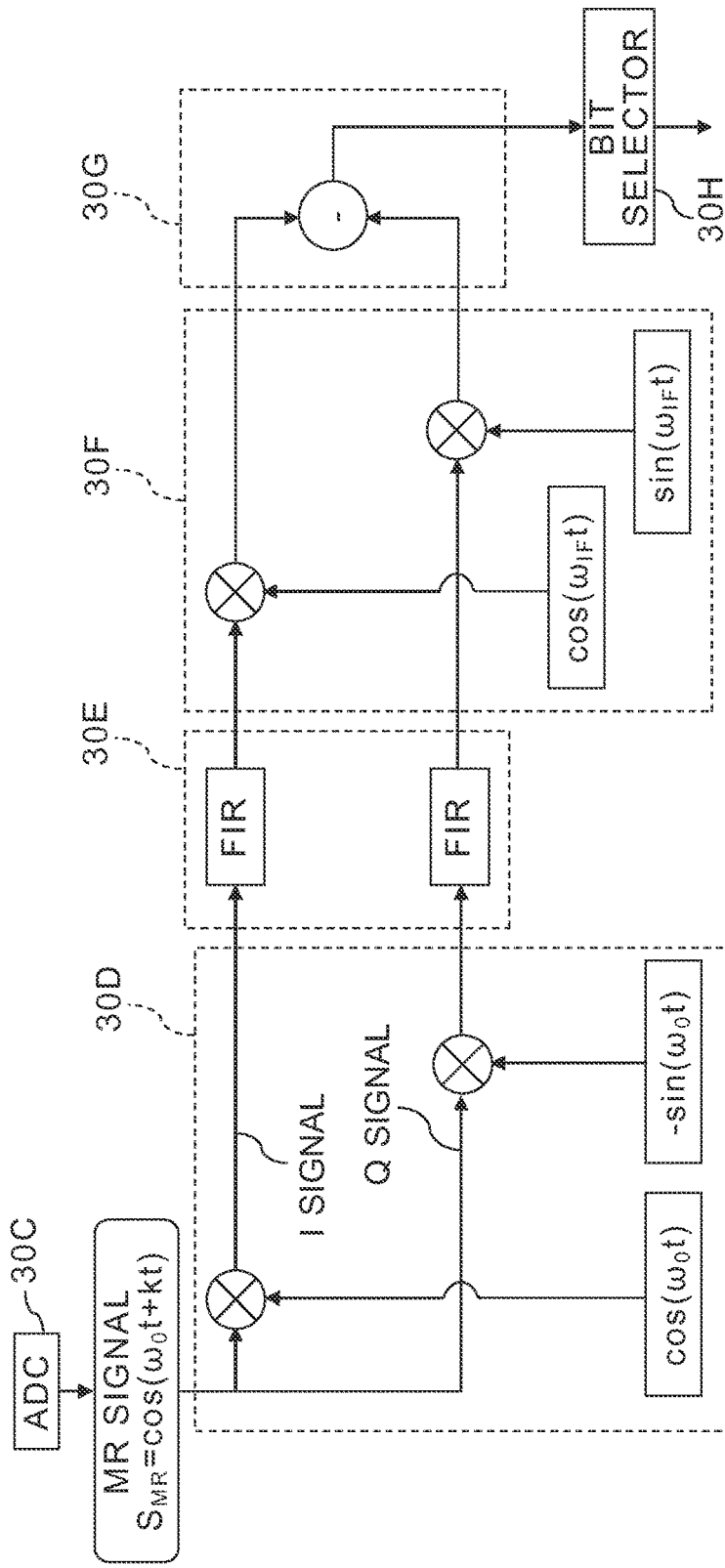
FIG. 4 is a block diagram showing a flow of signal processing of an MR signal after the A/D conversion in the receiver shown in FIG. 1.
Figure 5:
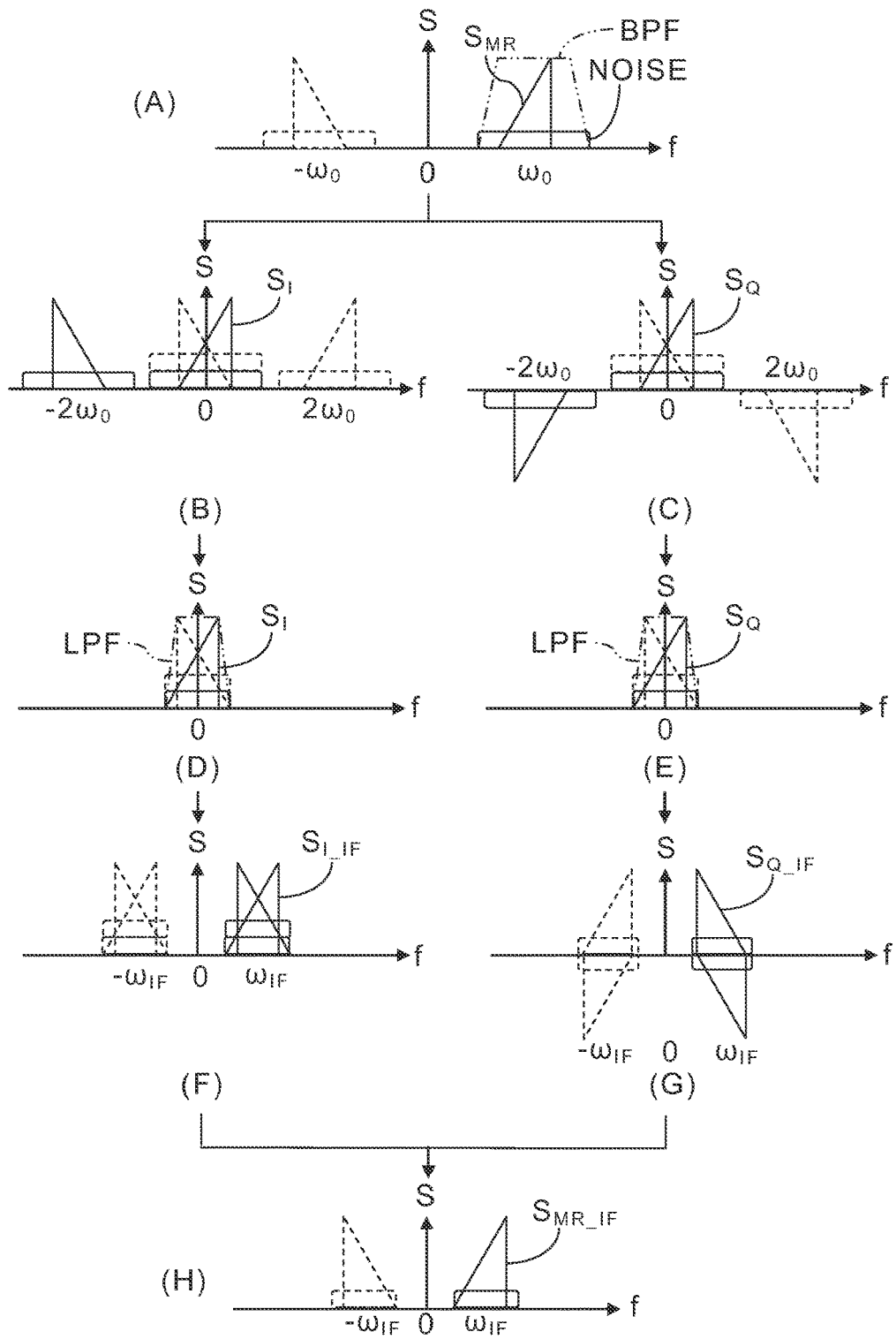
FIG. 5 is a schematic diagram showing waveforms of MR signals generated by the signal processing shown in FIG. 4.

FIG. 4 is a block diagram showing a flow of signal processing of an MR signal after the A/D conversion in the receiver 30 shown in FIG. 1, and FIG. 5 is a schematic diagram showing waveforms of MR signals generated by the signal processing shown in FIG. 4.

In each graph of FIG. 5, the vertical axis shows signal amplitude S, and the horizontal axis shows frequency f. The dotted lines in FIG. 5 show signals arising when it is assumed that the BPF processing is not performed before the A/D conversion of the MR signal.

As shown in (A) of FIG. 5, an MR signal $S_{MR} = \cos(\omega_0 t + kt)$ extracted by the BPF 30B from an MR signal received in a reception band of $\pm \omega_0$ is a target of the A/D conversion. Note that, k is a coefficient and t is time. Therefore, an digitized MR signal $S_{MR} = \cos(\omega_0 t + kt)$ is given to the downconversion/IQ separating part 30D, as shown in FIG. 4.

In the downconversion/IQ separating part 30D, the MR signal $S_{MR}$ is multiplied by $\cos(\omega_0 t)$. Thereby, an I signal $S_I = \cos(\omega_0 t + kt) \times \cos(\omega_0 t) = \cos(2\omega_0 t + kt) + \cos(kt)$ whose frequency is down-converted to the baseband is generated, as shown in (B) of FIG. 5. In addition, the MR signal $S_{MR}$ is multiplied by $-\sin(\omega_0 t)$. Thereby, a Q signal $S_Q = \cos(\omega_0 t + kt) \times -\sin(\omega_0 t) = -\sin(2\omega_0 t + kt) + \sin(kt)$ whose frequency is down-converted to the baseband is generated, as shown in (C) of FIG. 5.

Next, each of the I signal and the Q signal which have been generated in the downconversion/IQ separating part 30D is subjected to filter processing by a common LPF, such as an FIR filter, in the digital filter 30E. As a result of the filter processing, the I signal and the Q signal whose frequencies have been limited to the baseband are obtained as shown in (D) and (E) of FIG. 5, respectively.

In the digital filter 30E, it is desirable to perform filter processing by setting a target frequency band to a range of not less than $\Delta f_{MR}/2$ and not more than $\Delta f_{MR}$ wherein $\Delta f_{MR}$ is a frequency band of the target MR signal. Thereby, a folded noise resulting from the filter processing can be reduced.

The number of taps of the digital filter 30E can be reduced by performing the filter processing of an I signal and a Q signal with a decimation filter. The decimation filter is an LPF for down sampling in which a cutoff frequency is the Nyquist frequency. In a case of performing the filter processing with a decimation filter, it is also desirable to perform the filter processing by setting a target frequency band to a range of not less than $\Delta f_{MR}/2$ and not more than $f_{sd}/2$ wherein $f_{sd}$ is a sampling frequency after the decimation filter processing. Thereby, a folded noise resulting from the decimation filter can be reduced.

The I signal and the Q signal after the filter processing are given to the upconversion part 30F. In the upconversion part 30F, the I signal and the Q signal after the filter processing are multiplied by $\cos(\omega_{IF}t)$ and $\sin(\omega_{IF}t)$, respectively. Thereby, the I signal $S_{I\_IF}=\cos(\omega_{IF}t+kt)+\cos(\omega_{IF}t-kt)$ and the Q signal $S_{Q\_IF}=-\cos(\omega_{IF}t+kt)+\cos(\omega_{IF}t-kt)$, whose frequencies are up-converted to an IF (intermediate frequency), are generated respectively as shown in (F) and (G) of FIG. 5.

The up-converted I signal $S_{I\_IF}$ and the up-converted Q signal $S_{Q\_IF}$ are combined with each other in the IQ composition part 30G. Specifically, the up-converted Q signal $S_{Q\_IF}$ is subtracted from the up-converted I signal $S_{I\_IF}$. Thereby, an up-converted MR signal $S_{MR\_IF}=\cos(\omega_{IF}t+kt)+\cos(\omega_{IF}t-kt)-\{-\cos(\omega_{IF}t+kt)+\cos(\omega_{IF}t-kt)\}=\cos(\omega_{IF}t+kt)$ in which the I signal $S_{I\_IF}$ and the Q signal $S_{Q\_IF}$ as components have been combined with each other is generated as shown in (H) of FIG. 5.

As shown in (H) of FIG. 5, it can be confirmed that an up-converted MR signal, in which a folded noise has been canceled, can be generated by a series of the signal processing of an MR signal shown in FIG. 4. Each up-converted MR signal is output to elements, such as the sequence controller 31, through the bit selector 30H.

The MR signals output from the receiver 30 to the sequence controller 31 are input into the processing circuitry 35 of the computer 32 through the sequence controller 31. Then, MR image data are reconstructed based on the MR signals by image reconstruction processing in the processing circuitry 35 of the computer 32.

The respective carriers for reception detections of an I signal and a Q signal used for the above-mentioned downconversion and IQ separation in the downconversion/IQ separating part 30D are generated in the carrier generation part 30I for reception detection. Generation processing of a carrier for reception detection in the carrier generation part 30I for reception detection refers to a clock whose frequency has been divided in the frequency divider 29B.

Figure 6:
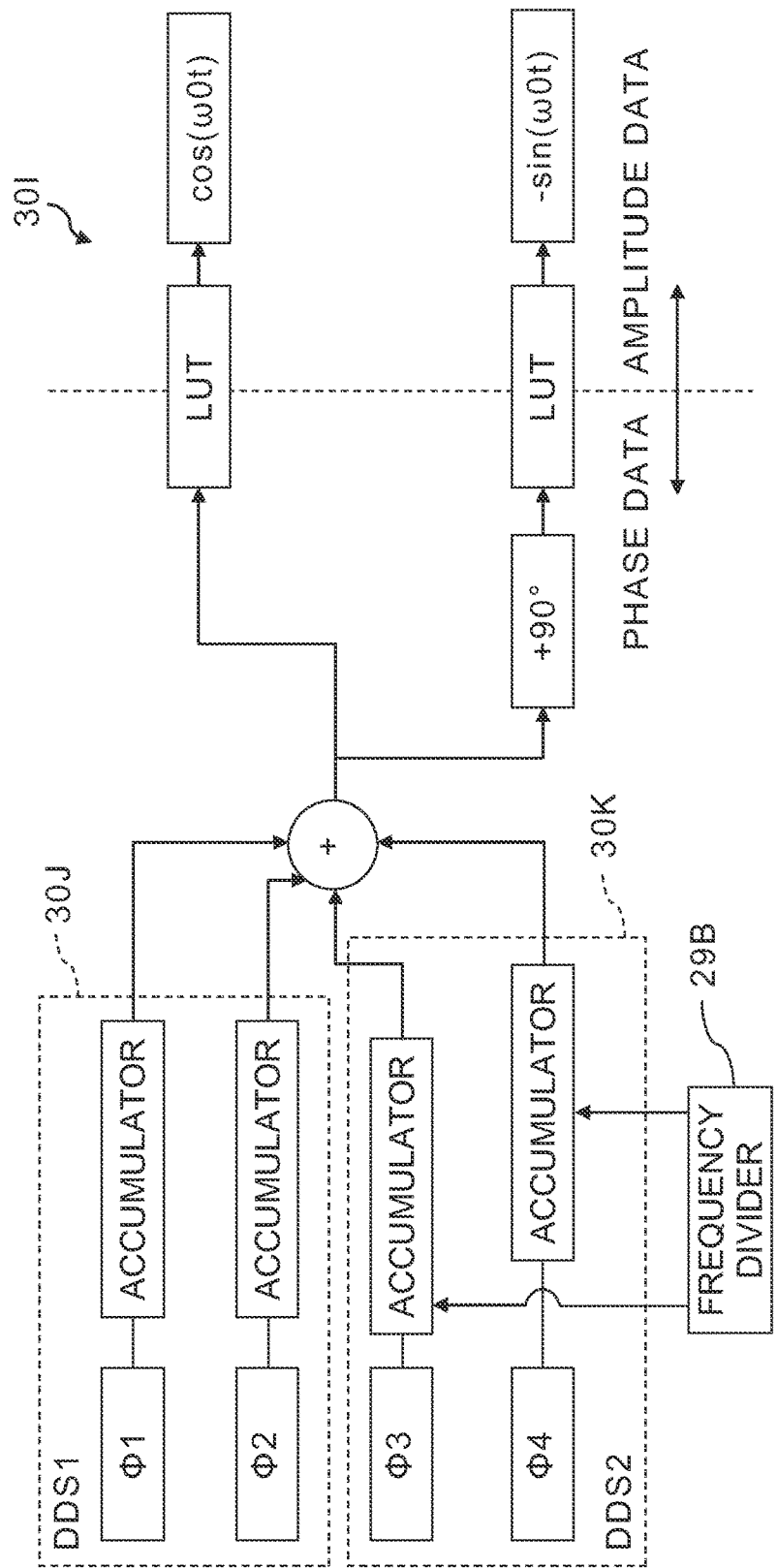
FIG. 6 is a diagram showing a method of generating a carrier for reception detection in the carrier generation part for reception detection shown in FIG. 2.

FIG. 6 is a diagram showing a method of generating a carrier for reception detection in the carrier generation part 30I for reception detection shown in FIG. 2.

As shown in FIG. 6, the first DDS 30J has the first phase setting part Φ1, the second phase setting part Φ2 and accumulators corresponding to the first phase setting part Φ1 and the second phase setting part Φ2, for generating a carrier for reception detection in the higher frequency side. Similarly, the second DDS 30K has the third phase setting part Φ3, the fourth phase setting part Φ4 and accumulators corresponding to the third phase setting part Φ3 and the fourth phase setting part Φ4, for generating a carrier for reception detection in the lower frequency side.

The phase values which are set in the first phase setting part Φ1 and the phase values which are set in the second phase setting part Φ2 are accumulated in the corresponding accumulators, respectively. Thereby, phase data sets in the higher frequency side whose frequencies are different from each other are generated. Similarly, the phase values which are set in the third phase setting part Φ3 and the phase values which are set in the fourth phase setting part Φ4 are also accumulated in the corresponding accumulators, respectively. Thereby, phase data sets in the lower frequency side whose frequencies are different from each other are generated.

The phase data sets generated in the first DDS 30J are used as a carrier for reception detection corresponding to a transmission carrier generated as a digital signal without the crystal oscillator 29A as the original oscillation, in the DDS 29C of the transmitter 29. A method of generating a carrier for reception detection in the first DDS 30J is same as a method of generating a transmission carrier in the DDS 29C of the transmitter 29.

Therefore, the first DDS 30J generates a carrier for reception detection having a frequency corresponding to a frequency of the transmission carrier generated in the frequency divider 29B of the transmitter 29. For that purpose, the first DDS 30J generates a carrier for reception detection with the same phase setting value as a phase setting value in the DDS 29C of the transmitter 29.

Meanwhile, the phase data sets generated in the second DDS 30K are used as a carrier for reception detection corresponding to a transmission carrier whose frequency has been divided, with the crystal oscillator 29A as the original oscillation, in the frequency divider 29B of the transmitter 29. Therefore, the second DDS 30K also generates a carrier for reception detection having a frequency corresponding to a frequency of the transmission carrier generated in the frequency divider 29B of the transmitter 29.

However, a method of generating a carrier by the frequency divider 29B differs from that by the second DDS 30K. Therefore, a phase error between the transmission carrier generated in the frequency divider 29B and the carrier for reception detection generated in the second DDS 30K is corrected. Specifically, a clock obtained from the frequency divider 29B is referred to by the respective accumulators of the second DDS 30K. Then, phase data in each accumulator are reset to zero at a predetermined timing based on the clock obtained from the frequency divider 29B. Thereby, a phase error accumulated by accumulation processing of phase values in each accumulator of the second DDS 30K can be reset to zero. Then, it becomes possible to synchronize a phase and a frequency of the transmission carrier with a phase and a frequency of the carrier for reception detection accurately.

A period and an interval to reset the phase data can be set according to a common divisor of a frequency of the clock obtained from the frequency divider 29B and a frequency of the carrier for reception detection which should be generated in each accumulator of the second DDS 30K. As a specific example, when a frequency of the clock, which has been derived by the frequency dividing of the original oscillation in the frequency divider 29B, is 100 MHz and a frequency of the carrier for reception detection which should be generated in the second DDS 30K is 2 MHz, the phase data can be reset with a clock in frequency, such as 2 MHz, 1 MHz, 0.5 MHz, . . . which are common divisors of 100 MHz and 2 MHz. That is, the phase data can be reset not only for every period but also for every n (n is a natural number) period.

As described above, the carrier generation part 30I for reception detection can generate a clock, for resetting the phase data generated in the second DDS 30K, by a frequency dividing of a clock generated with the crystal oscillator 29A as the original oscillation. In that case, the clock for resetting the phase data may have a frequency corresponding to a common divisor of a frequency of the clock generated with the crystal oscillator 29A as the original oscillation and a corrected frequency of a clock of each detection carrier which is a correction target of a phase error. Then, a phase error of each detection carrier which is a correction target can be corrected based on a clock generated by a frequency dividing.

Note that, spurious component (unnecessary signal component) arises by a reset of a phase error accumulated in each accumulator of the second DDS 30K. As a result, an SFDR (spurious-free dynamic range) becomes small. Thus, it is desirable to secure the sufficient number of bits of the phase accumulation processing in each accumulator of the second DDS 30K in order to reduce an influence of the spurious component.

That is, it is preferable to perform the phase accumulation processing for generating each detection carrier, which is a correction target of a phase error, with the number of bits set so that an influence of the spurious component arising in the corrected detection carrier due to a correction of the phase error becomes negligible, in the second DDS 30K. Thereby, it is possible to reduce an error between a frequency of the carrier for reception detection generated in the second DDS 30K and a frequency of the transmission carrier generated by frequency dividing, and also avoid an influence of the spurious component. As a result, an SNR (signal to noise ratio) can be secured.

The respective carriers for reception detection by frequency, generated as pieces of phase data in the first DDS 30J and the second DDS 30K respectively, are combined with each other by addition processing. The added phase data are converted into corresponding amplitude data $\cos(\omega_0 t)$ by referring to an LUT (look-up table) which relates pieces of phase data with pieces of amplitude data.

Meanwhile, the phase data added in the adder circuit are converted into phase data, whose phase differs from that of the original phase data by +90°, with a 90° hybrid. Then, the phase data whose phase have shifted by +90° are converted into corresponding amplitude data $-\sin(\omega_0 t)$ by referring to an LUT which relates pieces of phase data with pieces of amplitude data.

Next, the two pieces of amplitude data $\cos(\omega_0 t)$ and $-\sin(\omega_0 t)$, which have been generated in the carrier generation part 30I for reception detection and whose phases have shifted by +90° from each other, are given to the downconversion/IQ separating part 30D as carriers for reception detections of an I signal and a Q signal respectively. Thus, even when a method of generating a carrier for reception detection differs from a method of generating a transmission carrier, it becomes possible to perform more appropriate reception detections of an I signal and a Q signal by generating the carriers for the reception detections with correcting a phase error resulting from the difference between the methods of generating the carriers.

Note that, it is preferable to perform a correction of a phase error resulting from the difference between the methods of generating the carriers not only in the reception detection processing of an I signal and a Q signal but also in the upconversion of the detected I signal and Q signal into the IF.

More specifically, the respective frequencies of an I signal and a Q signal after the filter processing can be up-converted into the IF in the upconversion part 30F by multiplying functions $\cos(\omega_{IF} t)$ and $\sin(\omega_{IF} t)$, each of which is generated using a clock obtained by frequency dividing of a clock generated with the crystal oscillator 29A as the original oscillation, with the I signal and Q signal after the filter processing respectively. In that case, the functions $\cos(\omega_{IF} t)$ and $\sin(\omega_{IF} t)$ which are multiplied with the I signal and the Q signal for the upconversion can be generated by resetting a phase error using a clock signal obtained from the frequency divider 29B, similarly to the pieces of amplitude data $\cos(\omega_0 t)$ and $-\sin(\omega_0 t)$ generated as the carriers for reception detections.

The magnetic resonance imaging apparatus 20 as described above is configured to perform the A/D conversion of an analog MR signal directly without converting its frequency, to separate the MR signal into an I signal and a Q signal, and to perform filter processing of each of the I signal and the Q signal for removing noises. In addition, the magnetic resonance imaging apparatus 20 is configured to synchronize a carrier for reception detection of an MR signal, corresponding to a transmission carrier generated by frequency dividing, using a clock generated by the frequency dividing.

The conventional magnetic resonance imaging apparatus in which a direct sampling of MR signals is tried had a problem that noises fold by signal processing, such as A/D conversion, downconversion and digital filter processing. In order to reduce the folded noises, a method of multiplying MR signals before A/D conversion with a steep BPF can be considered. Alternatively, a method of repeating downconversion and digital filter processing of MR signals after A/D conversion alternately or simultaneously two or three times can also be considered.

However, it is necessary to overlap many filters in order to make the characteristic of a BPF steep. Therefore, the size of a BPF becomes large, which obstructs increase in reception channels of MR signals. Furthermore, overlapping many filters leads to an increase in cost of a BPF. Therefore, making the characteristic of a BPF steep is impractical.

On the other hand, repeating downconversion and digital filter processing of MR signals requires a large scale circuit for a large amount of digital processing. Therefore, repeating downconversion and digital filter processing of MR signals also leads to an increase in a size and a cost of circuits.

By contrast, according to the magnetic resonance imaging apparatus 20, folded noises can be removed with simple processing and configuration by a signal processing method of performing digital filter processing after the IQ separation of MR signals. Specifically, only performing downconversion and digital filter processing once can prevent noises folded by signal processing, such as the A/D conversion, the downconversion and the digital filter processing, from overlapping with each other. Furthermore, the necessity of installing a steep BPF for MR signals before the A/D conversion can also be avoided. In addition, since the digital filter processing is performed after the IQ separation, noises which cannot be removed by a BPF can be removed.

Moreover, the conventional magnetic resonance imaging apparatus which does not perform a direct sampling of MR signals generates a transmission carrier of RF signal and a carrier for reception detection of MR signal by a same circuit. Therefore, gaps in frequency and phase between the transmission carrier and the carrier for reception detection do not occur due to a factor other than the instability of the original oscillation.

However, when a transmission carrier and a carrier for reception detection are generated in different methods, gaps in frequency and phase occur between the transmission carrier and the carrier for reception detection. Namely, gaps in frequency and phase occur between the transmission carrier and the carrier for reception detection due to not only the instability of the original oscillation but also a difference in the generation methods thereof.

Especially, digitization in receptions of MR signals is more advanced than digitization in transmissions of RF signals in a magnetic resonance imaging apparatus in recent years. In this case, while a transmission carrier for RF signal is generated by only frequency dividing or both a DDS and the frequency dividing, a carrier for reception detection is possibly generated only by a DDS so that detection of each MR signal can be processed of a digital signal.

While frequency dividing is a method of outputting a synchronization signal having a frequency f/n from an input signal having a frequency f, a DDS generates a sine wave by adding phases for every clock. Therefore, errors according to the resolution (the number of bits) of a set phase value are accumulated in a DDS.

By contrast, according to the magnetic resonance imaging apparatus 20, even when generation methods of carriers for transmission and reception of signals differ from each other, frequencies and phases in the carriers for transmission and reception can be accurately synchronized with each other. Specifically, even when the carrier for reception detection is generated only by a DDS while a transmission carrier is generated by both frequency dividing and a DDS or only frequency dividing, an accumulative error in phase occurring in the carrier for reception detection can be reset. Thereby, the tunability between the transmission carrier and the carrier for reception detection can be kept. Then, image quality deterioration and a positional gap in an MR image can be prevented by suppressing gaps in frequencies and phases between the transmission carrier and the carrier for reception detection.

Second Embodiment

Figure 7:
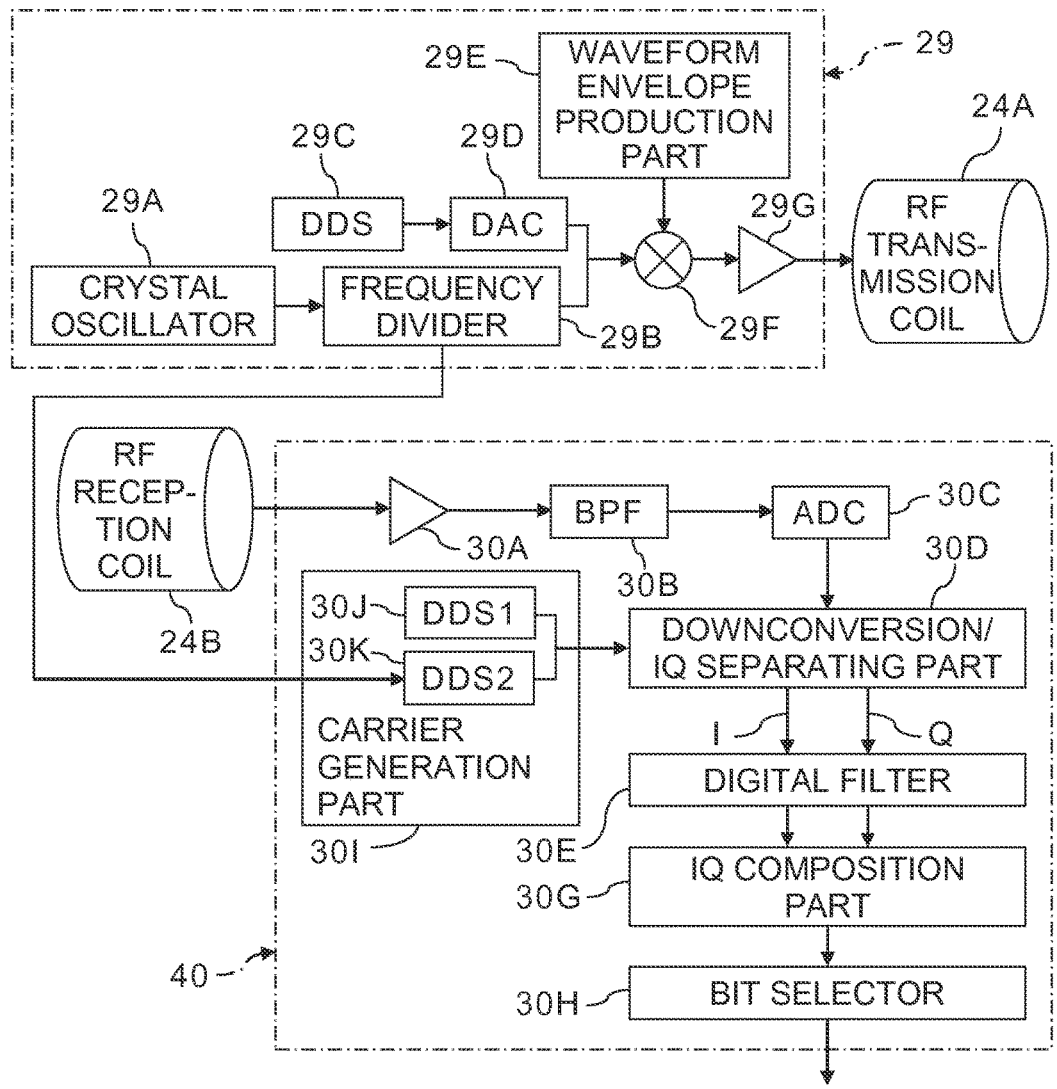
FIG. 7 is a functional block diagram showing each detailed configuration of a transmitter and a receiver included in a magnetic resonance imaging apparatus according to the second embodiment of the present invention.

FIG. 7 is a functional block diagram showing each detailed configuration of a transmitter and a receiver included in a magnetic resonance imaging apparatus according to the second embodiment of the present invention.

The magnetic resonance imaging apparatus in the second embodiment is different from the magnetic resonance imaging apparatus 20 in the first embodiment in a detail configuration of the receiver 40 composing the data acquiring system of MR signals. Other configurations and functions of the magnetic resonance imaging apparatus in the second embodiment do not substantially differ from those of the magnetic resonance imaging apparatus 20 in the first embodiment. Therefore, only detail configurations of the transmitter 29 and the receiver 40 are illustrated. The same configurations are shown with the same signs, and their explanations are omitted.

In the receiver 40 of the magnetic resonance imaging apparatus in the second embodiment, the downconversion/IQ separating part 30D is configured to convert MR signals after the A/D conversion into not I signals and Q signals, each having a frequency in the baseband, but I signals and Q signals, each having an intermediate frequency. That is, the downconversion/IQ separating part 30D down-converts the MR signals after the A/D conversion into MR signals having a desired frequency.

Meanwhile, output signals from the digital filter 30E are input into the IQ composition part 30G without going through the upconversion part 30F, in the receiver 40. Specifically, since a frequency of MR signal is down-converted into not a frequency in a baseband but a desired frequency appropriate for following signal processing the receiver 40, in the downconversion/IQ separating part 30D, the I signal and the Q signal after the filter processing in the digital filter 30E are combined with each other, without upconversion, in the IQ composition part 30G. Therefore, the receiver 40 functions as a composition part configured to combine the filter processed I signal with the filter processed Q signal without upconversion.

In this case, the filter processing is performed on the I signal and the Q signal, which have been down-converted into a predetermined frequency, using individual filters respectively in the digital filter 30E.

Figure 8:
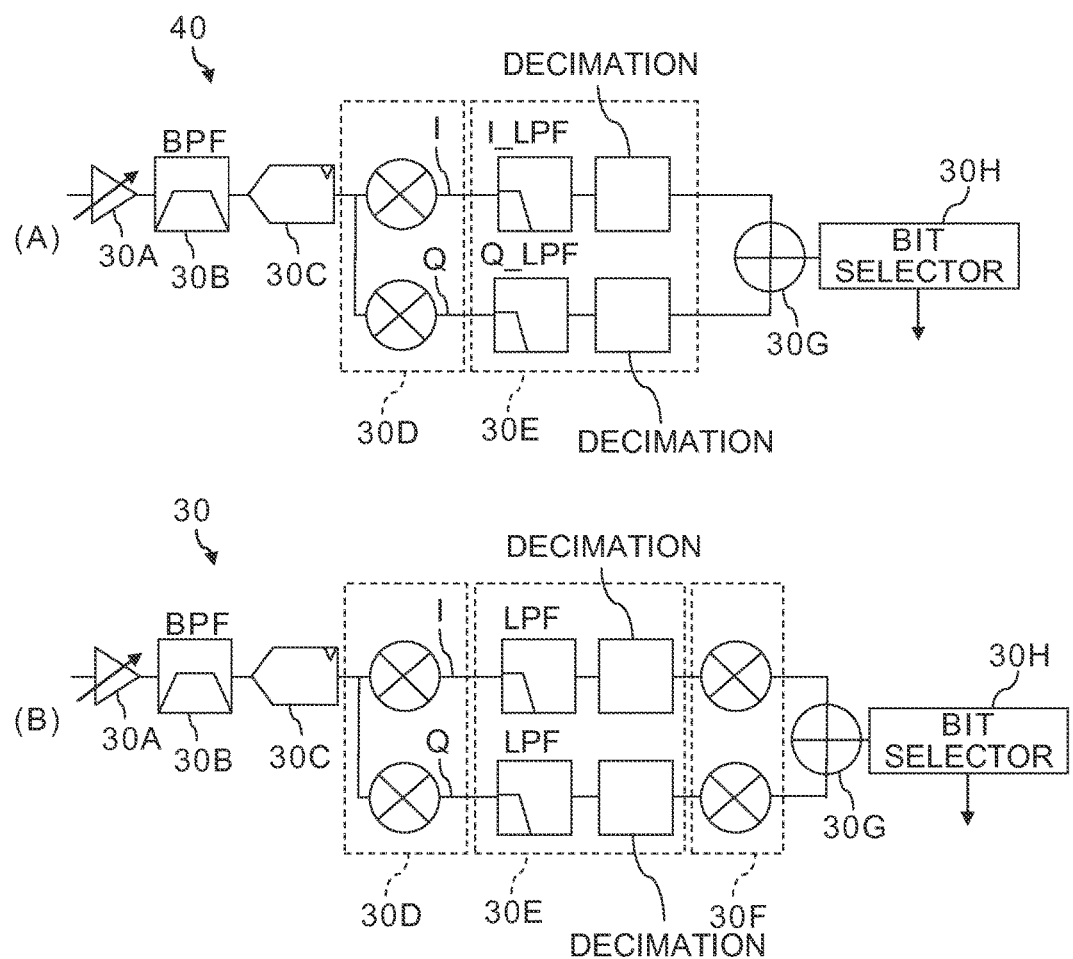
FIG. 8 shows an example of detailed configuration of the receiver in the second embodiment shown in FIG. 7, compared with an example of detailed configuration of the receiver in the first embodiment.

FIG. 8 shows an example of detailed configuration of the receiver 40 in the second embodiment shown in FIG. 7, compared with an example of detailed configuration of the receiver 30 in the first embodiment.

(A) of FIG. 8 shows an example of detailed configuration of the receiver 40 in the second embodiment. Meanwhile, (B) of FIG. 8 shows an example of detailed configuration of the receiver 30 in the first embodiment. As shown in (A) of FIG. 8, a frequency band of each analog MR signal amplified in the amplifier 30A is limited in the BPF 30B. Each analog MR signal which has gone through the BPF 30B is converted into a digital signal in the ADC 30C without frequency conversion. That is, a direct sampling of MR signal is performed.

Figure 9:
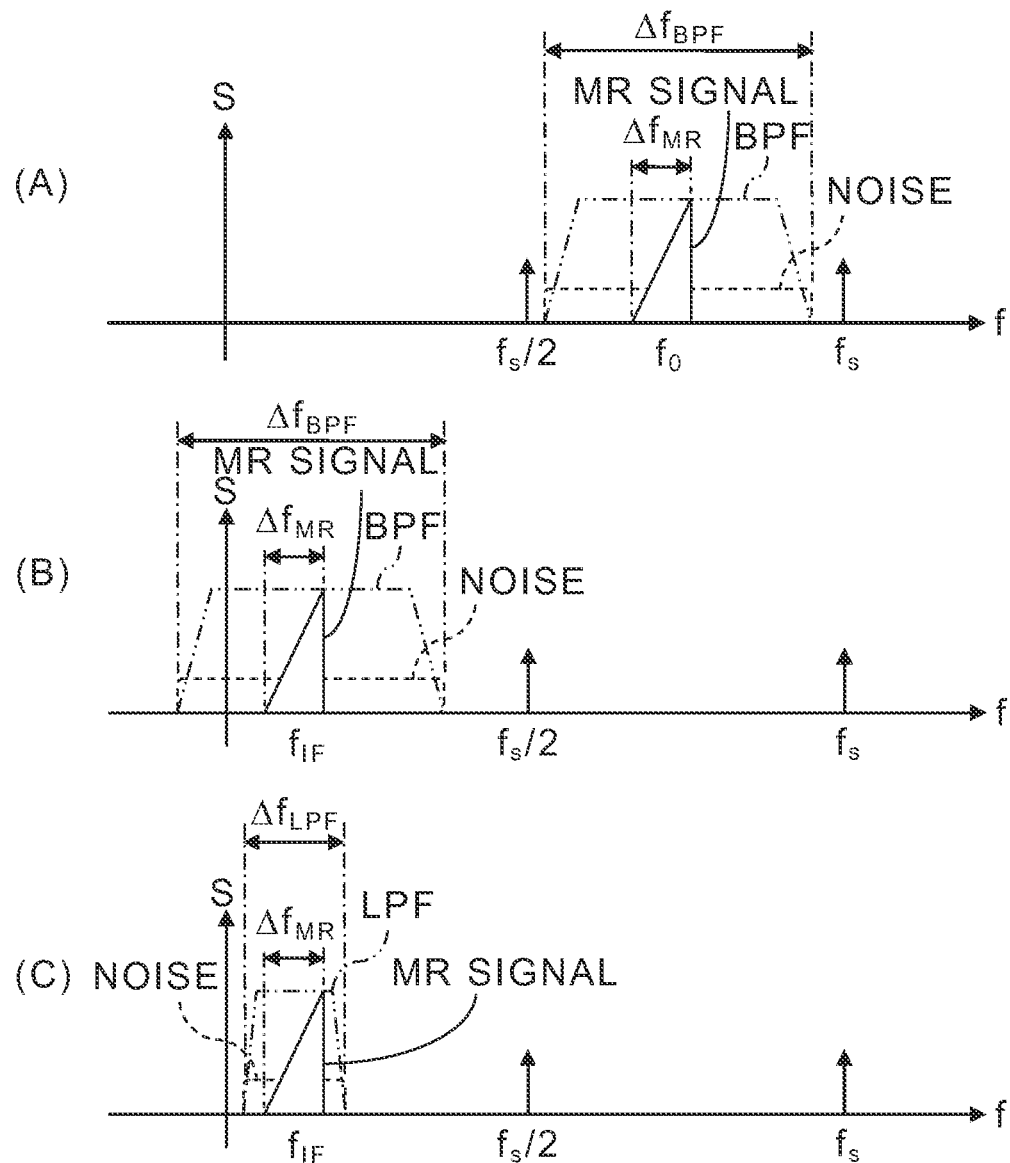
FIG. 9 shows schematic graphs showing frequency bands of MR signals generated by signal processing in the receiver shown in (A) of FIG. 8.

FIG. 9 shows schematic graphs showing frequency bands of MR signals generated by signal processing in the receiver 40 shown in (A) of FIG. 8.

In each of (A), (B) and (C) of FIG. 9, the vertical axis shows signal amplitude S, and the horizontal axis shows frequency f.

(A) of FIG. 9 shows a frequency band of an MR signal immediately after the sampling in the ADC 30C. As shown in (A) of FIG. 9, an MR signal whose center frequency is $f_0$ and frequency band is $\Delta f_{MR}$ is sampled with a sampling frequency $f_s$. Since the MR signal has gone through the BPF 30B before the sampling, a noise component exists in a frequency band $\Delta f_{BPF}$ of the BPF 30B.

The MR signal after the A/D conversion is down-converted into a signal having an intermediate frequency and separated into an I signal and a Q signal, in the downconversion/IQ separating part 30D. Specifically, carriers for reception detections of the I signal and the Q signal are multiplied by the MR signal, after the A/D conversion, by a mixer. As a result, the center frequency of the MR signal in which the noise component lies in the frequency band $\Delta f_{BPF}$ of the BPF 30B becomes the intermediate frequency $f_{IF}$, as shown in (B) of FIG. 9.

For example, when an intensity of static magnetic field is 1.5 [T], a frequency about 36 [MHz] is down-converted into an intermediate frequency of about 0.5 [MHz]. In this case, a sampling speed changes from 100 [MSPS] to about 2 [MSPS].

Each of the I signal and the Q signal, each having the intermediate frequency, generated in the downconversion/IQ separating part 30D is output to the digital filter 30E. When the digital filter 30E is composed by a decimation filter, the digital filter 30E can be expressed by an LPF and the decimation filter, as shown in (A) of FIG. 8.

Then, each of the I signal and the Q signal is filtered by the LPF and the decimation filter in the digital filter 30E. Thereby, a noise component is removed from each of the I signal and the Q signal. Specifically, the I signal and the Q signal in which the noise component has been limited within a frequency band $\Delta f_{LPF}$ of LPF are generated by the LPF which is a complex filter, as shown in (C) of FIG. 9.

The I signal and the Q signal which are output from the digital filter 30E are combined with each other in the IQ composition part 30G without upconversion. Then, an MR signal generated by the composition of the I signal and the Q signal in the IQ composition part 30G is output from the receiver 40 through the bit selector 30H.

Meanwhile, in the receiver 30 in the first embodiment, each of an I signal and a Q signal in which a frequency has been down-converted into a baseband which is the minimum frequency is generated in the downconversion/IQ separating part 30D. Therefore, the upconversion part 30F is installed in the latter part of the digital filter 30E, as shown in (B) of FIG. 8. Then, each of the I signal and the Q signal the after the filter processing, whose frequency has been down-converted into the baseband, is up-converted into an intermediate frequency in the upconversion part 30F.

As exemplified in (A) and (B) of FIG. 8, separating an MR signal into an I signal and a Q signal and the filter processing for removing a noise can be performed by various signal processing. As a result, overlap of noises due to the downconversion of an sampled MR signal into an intermediate frequency can be prevented. In other words, the digital filter processing can be performed so that noises do not overlap with each other due to the downconversion of an MR signal.

As described above, the magnetic resonance imaging apparatus in the second embodiment is configured to down-convert and separate an MR signal after the A/D conversion into an I signal and a Q signal each having an intermediate frequency, and subsequently to perform the filter processing of the I signal and the Q signal using individual filters respectively.

Therefore, according to the magnetic resonance imaging apparatus in the second embodiment, effects similar to those by the magnetic resonance imaging apparatus 20 in the first embodiment can be obtained. In addition, according to the magnetic resonance imaging apparatus in the second embodiment, a configuration of the receiver 40 and signal processing can be simplified.

Other Embodiments

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

For example, although the above-mentioned embodiments described examples to reset a phase error between a clock generated by frequency dividing and a clock generated by a DDS, a method for generating a clock is not limited to the frequency dividing. Specifically, a phase error between a clock generated in a method other than the DDS and a clock generated by the DDS can be reset based on the clock generated in the method other than the DDS. That is, the receiver 30 may have a function to correct a phase error of a clock of a detection carrier, which is generated in a generation method by a DDS, for each of an I signal and a Q signal, corresponding to an RF transmission signal in which clock of a transmission carrier is generated in a method other than the generation method by the DDS, among I signals and Q signals. In this case, the phase error of the clock of the detection carrier can be corrected based on a clock generated in the method other than the generation method by the DDS.

Furthermore, even when an MR signal is not separated into an I signal and a Q signal for the filter processing, a phase error of a detection carrier resulting from a difference of generation methods of clocks in a transmission and reception system can be corrected. Specifically, the receiver 30 may have a function to correct a phase error of a clock of a detection carrier, which is generated in a generation method by a DDS, for each MR signal, corresponding to an RF transmission signal whose clock of a transmission carrier is generated in a method other than the generation method by the DDS, among digital MR signals acquired by direct sampling. In this case, the phase error of the clock of the detection carrier can be corrected based on a clock generated in the method other than the generation method by the DDS.

Although each above-mentioned embodiment exemplifies a configuration in which the receiver 30 is connected to the RF reception coil 24B, the receiver 30 may be integrated with an RF reception coil 24B. Especially, when the RF reception coil 24B is a type of coil which transmits MR signals by wireless, the receiver 30 is usually an element of the RF reception coil 24B.

What is claimed is:

1. A magnetic resonance imaging (MRI) apparatus comprising:
　acquiring magnetic resonance signals from an object using a static field magnet, a gradient coil, at least one radio frequency coil and a receiver; and
　generating magnetic resonance image data based on the acquired magnetic resonance signals by
　configured to acquire magnetic resonance signals from an object; and
　　converting analog magnetic resonance signals received by said at least one radio frequency coil into digital magnetic resonance signals without a down conversion,
　　separating the digital magnetic resonance signals into in-phase signals and quadrature-phase signals,
　　performing filter processing in order to remove noise from the in-phase signals and the quadrature-phase signals, and
　　correcting phase errors of clocks of detection carriers for each in-phase signal and each quadrature-phase signal whose clock of a transmission carrier is generated by a method other than a method using a direct digital synthesizer, while the clocks of the in-phase and quadrature phase detection carriers are being generated using a direct digital synthesizer, with each of the phase errors being corrected based on a clock generated by the method other than the method using a direct digital synthesizer.

2. A magnetic resonance imaging (MRI) method comprising:
　acquiring magnetic resonance signals from an object using a static field magnet, a gradient coil, at least one radio frequency coil and a receiver; and
　generating magnetic resonance image data based on the acquired magnetic resonance signals by
　　converting analog magnetic resonance signals received by said at least one radio frequency coil into digital magnetic resonance signals without a down conversion,
　　separating the digital magnetic resonance signals into in-phase signals and quadrature-phase signals,
　　performing filter processing in order to remove noise from the in-phase signals and the quadrature-phase signals, and
　　performing an up conversion by multiplying functions with each in-phase signal and each quadrature-phase signal respectively, each of the functions being generated using a clock obtained by frequency dividing of a clock generated with a crystal oscillator as an original oscillation.

3. A magnetic resonance imaging (MRI) apparatus comprising:
a static field magnet, a gradient coil, at least one radio frequency coil and a receiver configured to acquire magnetic resonance signals from an object; and
processing circuitry configured to generate magnetic resonance image data based on the acquired magnetic resonance signals,
wherein said receiver is configured to
convert analog magnetic resonance signals received by said at least one radio frequency coil into digital magnetic resonance signals without a down conversion,
separate the digital magnetic resonance signals into in-phase signals and quadrature-phase signals,
perform filter processing in order to remove noise from the in-phase signals and the quadrature-phase signals, and
correct phase errors of clocks of detection carriers for each in-phase signal and each quadrature-phase signal whose clock of a transmission carrier is generated by a method other than a method using a direct digital synthesizer, while the clocks of the in-phase and quadrature phase detection carriers are being generated using a direct digital synthesizer, with each of the phase errors being corrected based on a clock generated by the method other than the method using a direct digital synthesizer.

4. A magnetic resonance imaging apparatus as in claim 3, wherein said receiver is configured to limit a frequency band of each of the analog magnetic resonance signals by a band pass filter whose a frequency band denoted by $\Delta f_{BPF}$ is set to satisfy $\Delta f_{BPF} < 4f_s - 4f_0 - \Delta f_{MR}$ and $\Delta f_{BPF} < 4f_0 - 2f_s - \Delta f_{MR}$ under a condition of $f_s/2 + \Delta f_{MR}R/4 < f_0 < f_s - \Delta f_{MR}/4$,
wherein $\Delta f_{MR}$ is the frequency band of each of the analog magnetic resonance signals input into the band pass filter, $f_0$ is a center frequency of the each of the analog magnetic resonance signals, and $f_s$ is a sampling frequency of the each of the analog magnetic resonance signals.

5. A magnetic resonance imaging apparatus, as in claim 3, wherein said receiver is configured to perform the filter processing of the in-phase signals and the quadrature-phase signals, each of the in-phase signals and the quadrature-phase signals being down-converted into a predetermined frequency before the filter processing, the in-phase signals being subjected to the filter processing using a first specific filter, the quadrature-phase signals being subjected to the filter processing using a second specific filter.

6. A magnetic resonance imaging apparatus of claim 5, wherein said receiver is configured to combine the in-phase signals with the quadrature-phase signals, after the filter processing, without an up conversion.

7. A magnetic resonance imaging apparatus, as in claim 3, wherein said receiver is configured to perform the filter processing of the in-phase signals and the quadrature-phase signals, using a common filter, each of the in-phase signals and the quadrature-phase signals being down-converted into a baseband before the filter processing.

8. A magnetic resonance imaging apparatus of claim 7, wherein said receiver is configured to combine the in-phase signals with the quadrature-phase signals, after an up conversion of the in-phase signals and the quadrature-phase signals, having been subjected to the filter processing, into a predetermined frequency.

9. A magnetic resonance imaging apparatus as in claim 3, wherein said receiver is configured to perform the filter processing of a target frequency band within a range of not less than $\Delta f_{MR}/2$ and not more than $\Delta f_{MR}$,
wherein $\Delta f_{MR}$ is a frequency band of each of the analog magnetic resonance signals.

10. A magnetic resonance imaging apparatus as in claim 3,
wherein said receiver is configured to perform the filter processing using a decimation filter.

11. A magnetic resonance imaging apparatus of claim 3, wherein said receiver is configured to correct phase errors of clocks of detection carriers for each in-phase signal and each quadrature-phase corresponding to a radio frequency transmission signal whose a clock of a transmission carrier is generated by frequency dividing of a clock generated with a crystal oscillator as an original oscillation, the clocks of the detection carriers being generated by the direct digital synthesizer, each of the phase errors being corrected based on a clock generated by frequency dividing.

12. A magnetic resonance imaging apparatus of claim 11, wherein said receiver is configured to
generate a clock, having a frequency which is a common divisor of a frequency of the clock generated with the crystal oscillator as the original oscillation and a corrected frequency of each clock of the detection carriers, based on the frequency dividing, and
correct each of the phase errors based on the clock generated by the frequency dividing.

13. A magnetic resonance imaging apparatus of claim 11, wherein said receiver is configured to perform phase accumulation processing for generating the detection carriers, with bits whose number is set to make an influence of a spurious component negligible, the spurious component arising, in each of corrected detection carriers, due to correcting each of the phase errors, the phase accumulation processing being performed in the direct digital synthesizer.

14. A magnetic resonance imaging (MRI) apparatus comprising:
a static field magnet, a gradient coil, at least one radio frequency coil and a receiver configured to acquire magnetic resonance signals from an object; and
processing circuitry configured to generate magnetic resonance image data based on the acquired magnetic resonance signals,
wherein said receiver is configured to
convert analog magnetic resonance signals received by said at least one radio frequency coil into digital magnetic resonance signals without a down conversion,
separate the digital magnetic resonance signals into in-phase signals and quadrature-phase signals,
perform filter processing in order to remove noise from the in-phase signals and the quadrature-phase signals, and
perform an up conversion by multiplying functions with each in-phase signal and each quadrature-phase signal respectively, each of the functions being generated using a clock obtained by frequency dividing of a clock generated with a crystal oscillator as an original oscillation.

\* \* \* \* \*